(12) United States Patent
Fortson et al.

(10) Patent No.: US 9,259,552 B2
(45) Date of Patent: Feb. 16, 2016

(54) MULTI-LUMEN CATHETER

(71) Applicant: Abbott Cardiovascular Systems Inc., Santa Clara, CA (US)

(72) Inventors: Aaron M. Fortson, Fremont, CA (US); Marc Gianotti, Wiesendangen (CH); David Milazzo, Santa Clara, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 369 days.

(21) Appl. No.: 13/843,363

(22) Filed: Mar. 15, 2013

(65) Prior Publication Data
US 2014/0081134 A1    Mar. 20, 2014

Related U.S. Application Data

(60) Provisional application No. 61/702,189, filed on Sep. 17, 2012.

(51) Int. Cl.
*A61B 1/00* (2006.01)
*A61M 5/315* (2006.01)
*A61M 25/00* (2006.01)
A61B 1/04 (2006.01)
A61M 25/09 (2006.01)
A61M 31/00 (2006.01)

(52) U.S. Cl.
CPC ......... *A61M 25/0026* (2013.01); *A61M 25/003* (2013.01); *A61M 25/007* (2013.01); *A61M 25/09* (2013.01); *A61M 31/005* (2013.01); *A61M 2025/0039* (2013.01); *A61M 2025/0076* (2013.01)

(58) Field of Classification Search
CPC ............. A61M 2025/0004; A61M 2025/0006; A61M 2025/0018; A61M 2025/0039; A61M 25/0074; A61M 25/75; A61M 2025/0079; A61M 2039/224

USPC ................. 600/435, 104, 114, 154; 604/102.01–102.03, 103.01, 103.03, 604/164.02, 236
See application file for complete search history.

(56) References Cited

U.S. PATENT DOCUMENTS

| 3,888,249 A | 6/1975 | Spencer |
| 4,927,418 A | 5/1990 | Dake et al. |
| 5,425,723 A | 6/1995 | Wang et al. |

(Continued)

FOREIGN PATENT DOCUMENTS

WO    01/51116 A2    7/2001

OTHER PUBLICATIONS

PCT International Search Report dated Aug. 27, 2013.

*Primary Examiner* — Anhtuan T Nguyen
*Assistant Examiner* — Timothy J Neal
(74) *Attorney, Agent, or Firm* — Fulwider Patton LLP

(57) ABSTRACT

A catheter comprising a first lumen for receiving a guidewire and having an exit opening at a distal tip of the catheter. A second lumen, adjacent the first lumen and separated from the first lumen by a common wall, the second lumen configured for receiving contrast fluid, wherein perforations are formed in the common wall; a guidewire in the first lumen the guidewire being configured to be capable of advancement distally to extend out of the exit opening, the guidewire having two conditions: a first condition in which the guidewire is advanced distally to block the perforations whereby fluid may not flow from the second lumen to the first lumen; a second condition in which the guidewire is withdrawn proximally to unblock the perforations whereby fluid may flow from the second lumen into the first lumen and thence out of the exit opening.

9 Claims, 5 Drawing Sheets

(56) References Cited

U.S. PATENT DOCUMENTS

| | | | |
|---|---|---|---|
| 5,833,706 A * | 11/1998 | St. Germain et al. | 606/194 |
| 6,206,849 B1 | 3/2001 | Martin et al. | |
| 7,569,046 B2 | 8/2009 | Zhou | |
| 2005/0288632 A1 | 12/2005 | Willard | |
| 2009/0198216 A1 * | 8/2009 | Muni et al. | 604/514 |
| 2009/0254062 A1 | 10/2009 | McGlothlin | |

* cited by examiner

US 9,259,552 B2

MULTI-LUMEN CATHETER

CROSS-REFERENCES TO RELATED APPLICATIONS

This application claims priority from U.S. Provisional Application No. 61/702,189, filed Sep. 17, 2012 incorporated by reference in its entirety.

BACKGROUND

The present invention relates to catheters for performing medical and surgical procedures inside cavities of a mammalian body. Specifically, the invention relates to a structure and method for arranging lumens in a catheter that are configured for transporting surgical devices and fluids required for performing a procedure at the distal end of the catheter.

Multi-lumen catheters have come into widespread use for conducting procedures inside cavities of the body. As a result, some catheters known in the art may have four lumens or more, providing for the transportation of liquids up and down the catheter, for one or more guide wires, and for a surgical device such as a rotating drill, or cutting element. Each lumen occupies space, and causes the catheter to assume an ever larger outside dimension. This is disadvantageous, especially at the distal end of the catheter where body lumens may be narrow.

Thus, there is a need in the art for a catheter that makes more efficient use of lumens that extend over the length of the catheter. This invention addresses these, and other needs.

SUMMARY OF THE INVENTION

In a preferred embodiment, the invention comprises a catheter having a first lumen for receiving a guidewire, the first lumen having an exit opening at a distal tip of the catheter. The catheter includes a second lumen, adjacent the first lumen and separated from the first lumen by a common wall, the second lumen configured for receiving contrast fluid. Perforations are formed in the common wall. A guidewire is positioned in the first lumen, the guidewire being configured to be capable of advancement distally to extend out of the exit opening, the guidewire having two conditions, namely: a first condition in which the guidewire is advanced distally to block the perforations whereby fluid may not flow from the second lumen to the first lumen; and, a second condition in which the guidewire is withdrawn proximally to unblock the perforations whereby fluid may flow from the second lumen into the first lumen and thence out of the exit opening.

In some embodiments, the first lumen is an internal lumen, and the second lumen is an external lumen. In further embodiments, a seal is provided in the first lumen to block fluid flowing proximally in the first lumen. In some embodiments, the seal is an O-ring seal. However, in other embodiments, no seal is provided and fluid may also flow proximally around the guidewire. However, it can be appreciated that the presence of the guidewire in the inner lumen will tend to compel most of the fluid to flow distally out of the distal tip exit.

In some embodiments, the catheter may include an outer cylinder that defines a plurality of openings that are configured to permit contrast fluid to flow from the second cylinder to a space external to the second cylinder. Such an arrangement may be utilized where additional contrast fluid is required. In some embodiments, the openings may have a slitted form, and are configured to be normally closed. In other embodiments, the openings may be circular.

In a further aspect, the invention is a method for discharging fluid from a distal end of a catheter. The method comprises advancing a guidewire distally through a first lumen of the catheter, and advancing fluid through a second lumen of the catheter. Initially, flow of the fluid from the second lumen into the first lumen is blocked, using the guidewire to block the flow. Then, the flow of fluid from the second lumen into the first lumen is unblocked by withdrawing the guidewire proximally, and causing the fluid to flow from the second lumen to the first lumen, and thence out of the distal end of the catheter.

These and other advantages of the invention will be understood by reference to the drawings and the detailed description of the preferred embodiments.

DETAILED DESCRIPTION OF THE PREFERRED EMBODIMENTS

Figure 1:
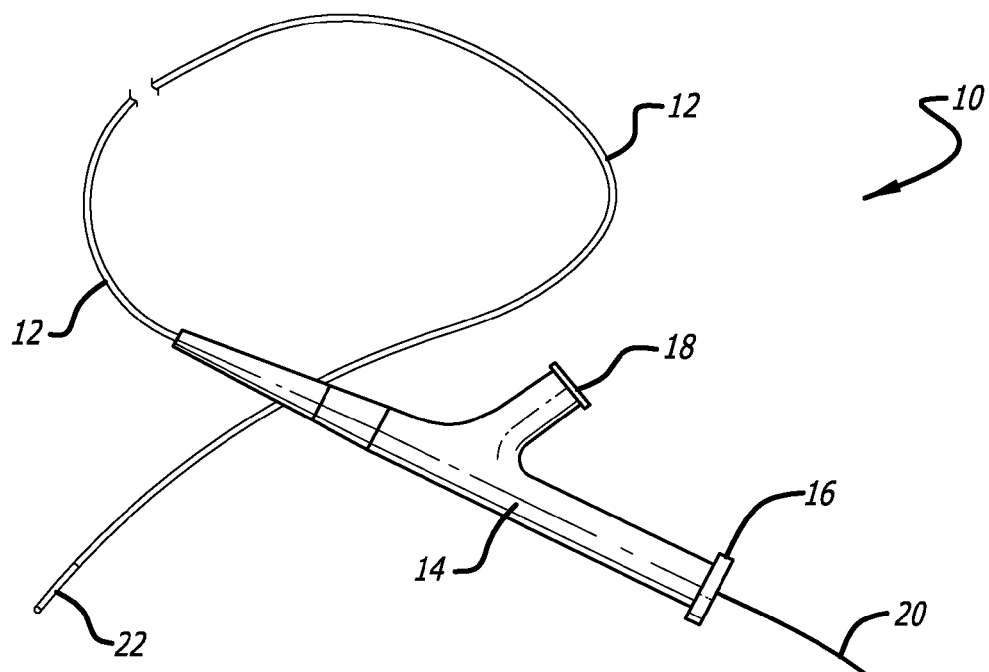
FIG. 1 is a general schematic view of a catheter having features of the invention.

With reference to the figures, there is described a catheter having features of the present invention. FIG. 1 shows a catheter system generally identified by the numeral 10. The catheter system includes a flexible element 12 for insertion into the patient's body by known means, and a handle 14 for controlling the operation of the flexible element 12. The handle includes a first luer connector 16 for insertion of a guide-wire, and a second luer connector 18 for introducing contrast liquid. A guide-wire 20 is configured for sliding insertion into the handle and along the flexible element 12.

The catheter 10 may be made of any suitable biocompatible material. In certain embodiments, catheter 10 is formed of polyurethane, which may include aliphatic or aromatic polyurethane. However, catheter 10 may alternatively be made of any suitable polymer such as polyamides, polyesters, polyolefins, fluoropolymer (such as fluorinated ethylene propylene (FEP), polytetrafluoroethylene (PTFE), perfluoroalkoxy (PFA), polyvinylidene fluoride (PVDF)), polyvinyl chloride (PVC), silicones (poly-dimethyl Siloxane), and so forth, as well as combinations. A number of manufacturing assemblies and procedures may be employed to make catheter 10. For example, catheter 10 may be made by injection molding which is a manufacturing process for forming objects, utilizing thermoplastic or thermoset plastics, metals, or ceramic materials, by heating the molding material and injecting it into a mold. During injection molding, a molding material or resin is shaped to form a desired part or object. Most polymers, including thermoplastics, thermosets, and elastomers, may be used as molding materials.

Figure 2A:
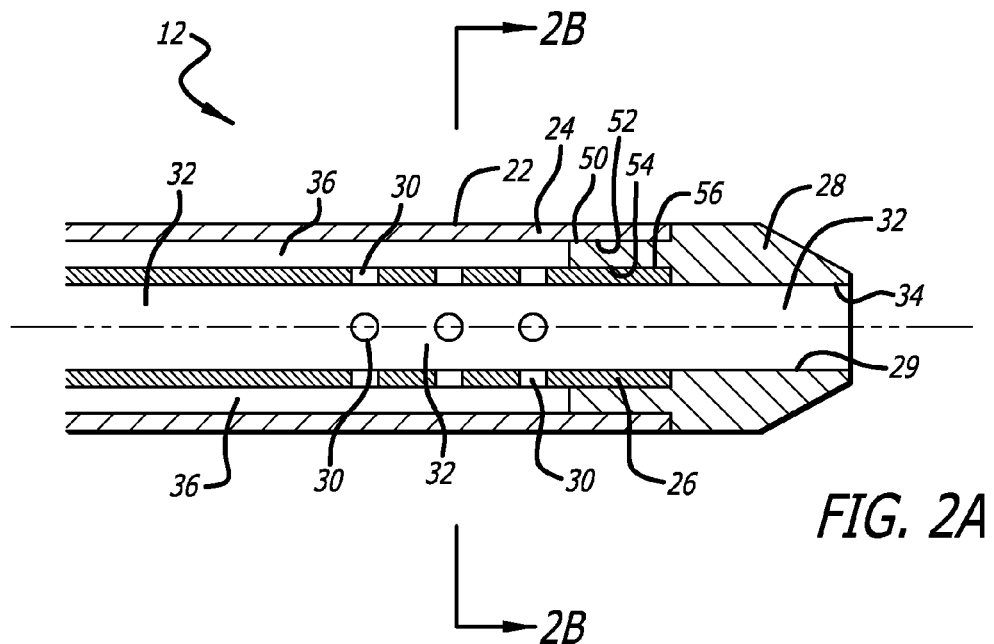
FIG. 2A is a sectional view of a distal end of the catheter.
Figure 2B:
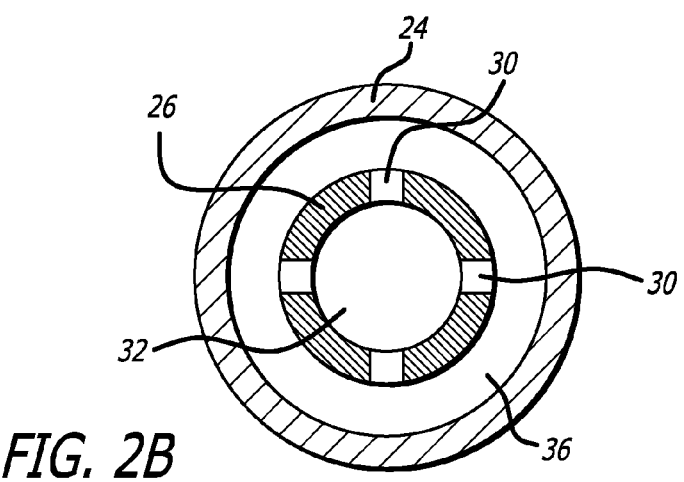
FIG. 2B is a sectional view taken substantially through the line 2B-2B in FIG. 2A.

FIGS. 2A and 2B exemplify the distal end 22 of the flexible element 12. At the distal end 22, the flexible element comprises an outer cylinder 24, and an inner cylinder 26 sized and configured for receiving the guide-wire 20. A distal tip 28 having an internal bore 29 may be connected to the outer cylinder 24, preferably by inserting an outer diameter portion 50 of the distal tip 28 into an internal diameter portion 52 of the outer cylinder 24 to provide a leak proof seal between distal tip and outer cylinder. The distal tip 28 may also be connected to the inner cylinder 26, by inserting an outer diameter portion 54 of the inner cylinder 26 into an inner diameter portion 56 of the distal tip 28, to provide a leak proof seal between distal tip and inner cylinder 26.

Figure 5A:
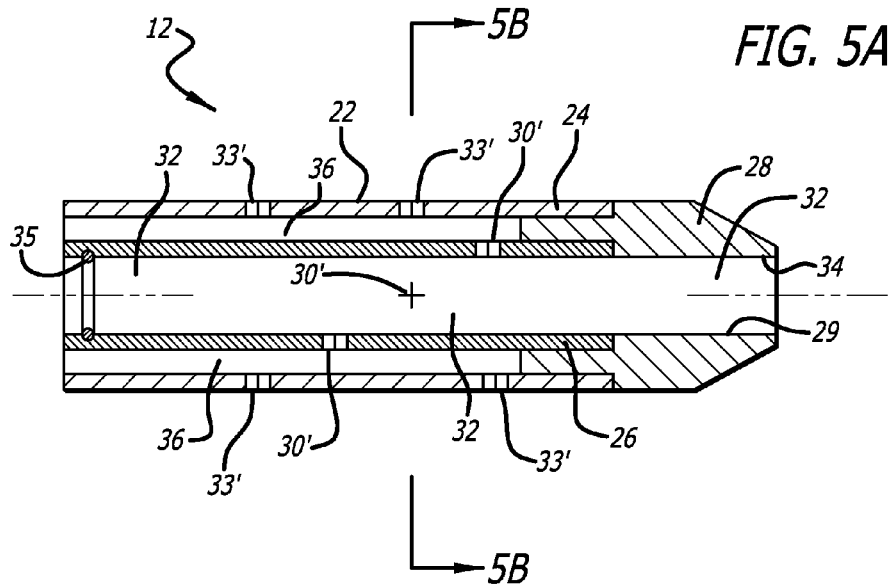
FIG. 5A is a sectional view of another embodiment of the catheter.
Figure 5B:
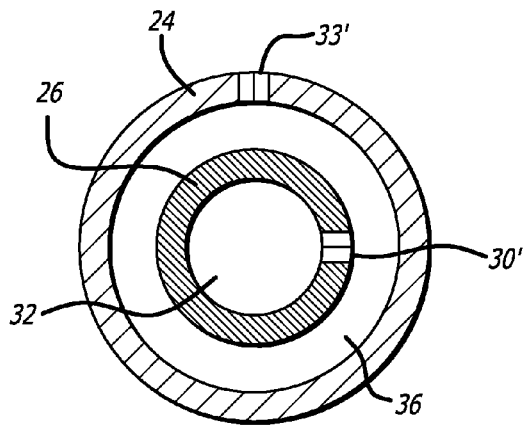
FIG. 5B is a sectional view taken substantially through the line 5B-5B in FIG. 5A
Figure 5C:
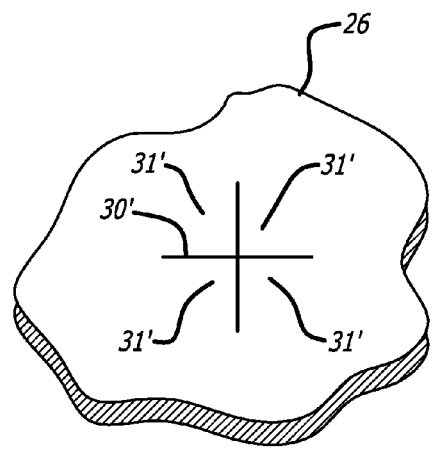
FIG. 5C is a plan view on an optional embodiment of a perforation used in the catheter.

At the distal end 22 of the flexible portion 12, small openings 30 or perforations are formed in a wall of the inner cylinder, as seen in FIGS. 2A and 2B. The openings may be formed by laser cutting or by punch cutting, and in one embodiment (seen in FIG. 2A) they may be circular. In another embodiment, openings 30' may be created in the wall of the inner cylinder, and may be given a slitted form. In this embodiment, exemplified in FIGS. 5A-5C, two intersecting slits may be cut into the wall of the inner cylinder 26 to produce four leaves 31' which occupy each of four quadrants around a center point as seen in FIG. 5C. In this configuration, the leaves may be flexible between open and closed conditions.

In one embodiment, the leaves 30' may be configured to maintain the slitted opening 30' in a "normally closed" condition—that is to say, the slitted openings are closed against each other and obstruct fluid flow when no forces are acting upon the leaves, while a force is required to open the leaves. In another embodiment, the leaves may be configured to maintain the slitted opening in a "normally open" condition—that is to say, the slitted openings are open and permit fluid flow when no forces are acting upon the leaves, while a force is required to close the leaves. A normally open condition may be created by applying heat to the slitted opening simultaneously with forcing the leaves to an open condition. Such may be accomplished by transmitting heated air, or fluid, through the openings and then rapidly transmitting chilled air or fluid to "set" the leaves in the open condition. The implications of these embodiments will be described below.

In some embodiments, each opening 30 (or 30') follows the preceding opening down an axial path with an offset angle to provide a helical pattern to the openings and thereby maintain the structural integrity of the inner cylinder 26. In some embodiments the offset angle is 90 degrees. In other embodiments, openings may be more numerous where the strength of the inner cylinder allows.

Figure 3:
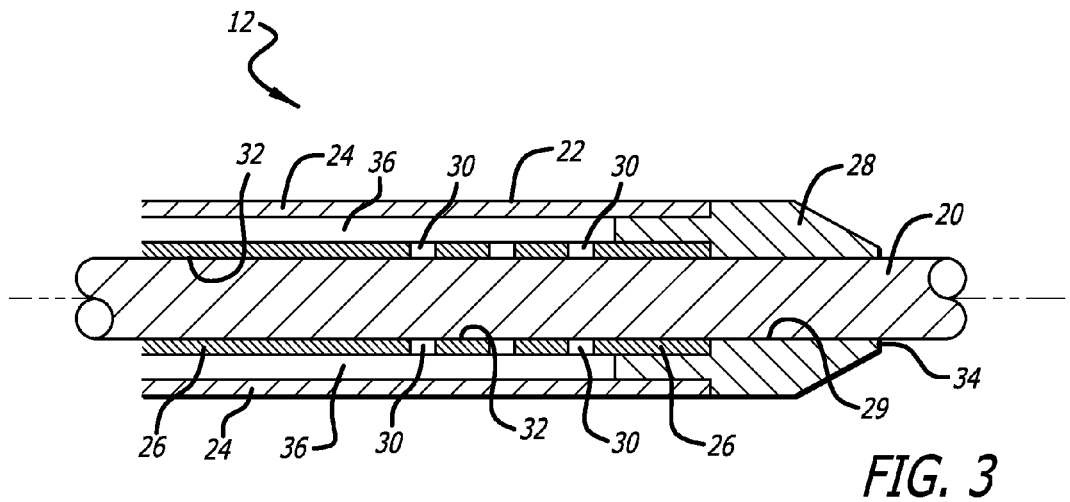
FIG. 3 is the view of FIG. 2A, shown with a guidewire in a first condition.

The resulting configuration of the distal end 22 of the flexible portion provides a structure in which the inner cylinder 26 defines an inner lumen 32 suitable for receiving the guidewire 20. The guidewire may extend from the handle 14 all the way up the inner lumen 32, and out of the bore 29 of the distal tip 28, through a distal opening 34 in the flexible portion of the catheter. In the space between the inner cylinder 26 and the outer cylinder 24, an outer lumen 36 is defined. Contrast fluid may pass under pressure from the handle (via contrast luer 18 by known pressurization means) all the way up the outer lumen 36 until it reaches the distal end 22 of the flexible portion 12. Once fluid has passed up the outer lumen, it may be confronted by either of two conditions:

In a first condition of the catheter, as shown in FIG. 3, the guidewire 20 may be positioned distally beyond the distal end 34 within the inner lumen 32, and in this condition may tend to block off the openings 30 (or 30') in the wall of the inner cylinder. In this condition, the contrast fluid in the outer lumen 36 is blocked from passing through the openings 30 (or 30') into the inner lumen 32.

Figure 4:
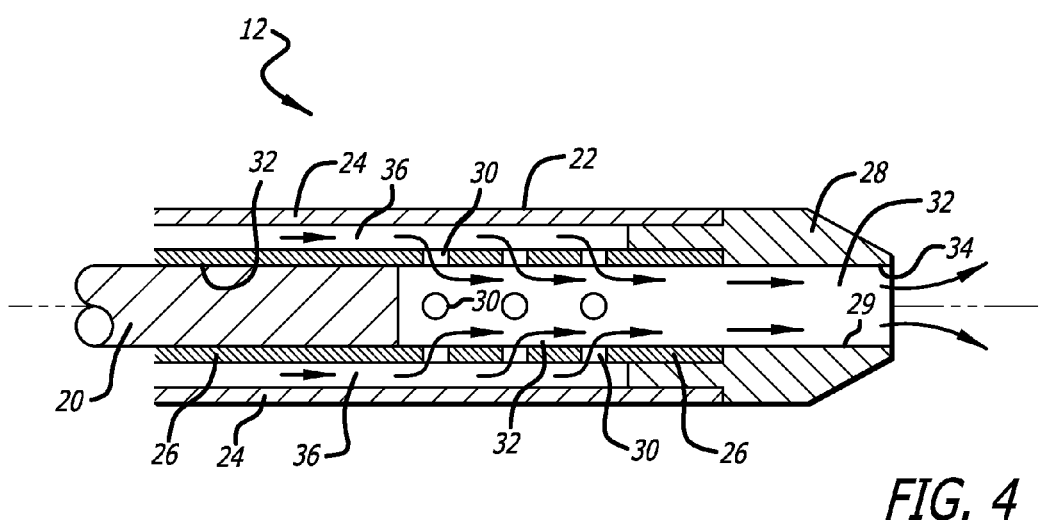
FIG. 4 is the view of FIG. 2A, shown with a guidewire in a second condition.

However, in a second condition of the catheter, as shown in FIG. 4, the guidewire 20 may be withdrawn proximally along the inner lumen 32, so that the openings 30 (or 30') in the wall of the inner cylinder are not blocked. In this condition, the contrast fluid that has been introduced under pressure up the outer lumen 36 may pass from the outer lumen 36 through the openings 30 (or 30') into the inner lumen 32, as shown by the arrows in FIG. 4. Here, the guidewire 20 merely blocks the passage of the fluid in a proximal direction along the inner lumen 32, from a location proximal to the openings 30 (or 30'), and thus compels the contrast liquid to flow distally, out of the distal tip 29 and out of the distal opening 34 of the catheter. To enhance the effectiveness of this fluid flow action, the guidewire 20 may be caused to pass through a valve that seals the perimeter of the guidewire to the internal diameter wall of the inner cylinder 26 so that proximal flow of the fluid is prevented. Such a valve may be positioned in the handle 14 at the guidewire luer 16, or may be positioned distally comprising a rubber gasket or O-ring 35 (FIG. 5A) through which the wire must pass, and which seals the perimeter of the guidewire against fluid flow in a proximal direction along inner lumen. In some embodiments, the seal is an O-ring seal. However, in other embodiments, no seal is provided and fluid may also flow proximally around the guidewire. It can be appreciated that the presence of the guidewire in the inner lumen will tend to compel most of the fluid in the inner lumen to flow distally out of the distal tip exit.

Figure 6:
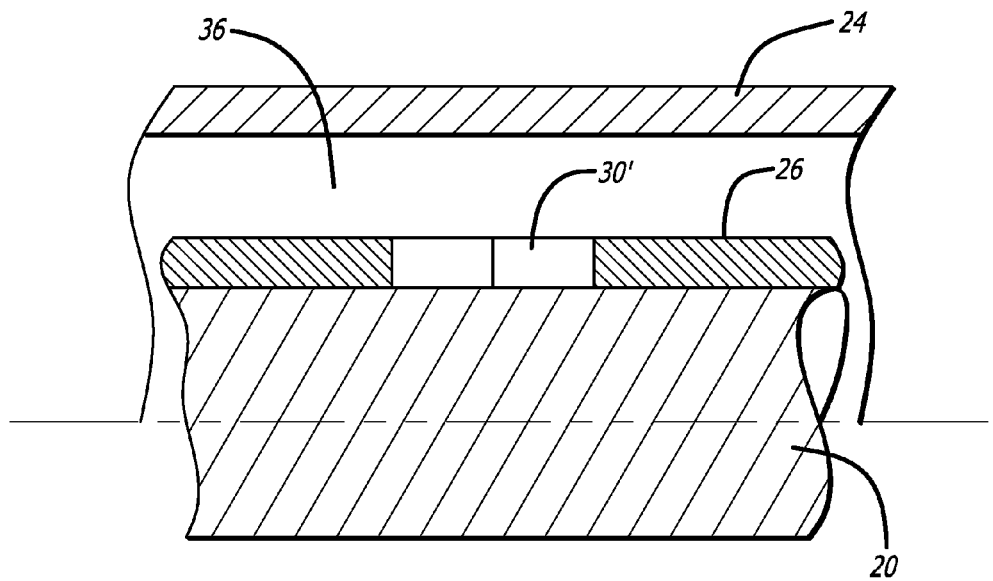
FIG. 6 is a detail view of an embodiment of a perforation used in the area marked "X" in FIG. 5A, shown with a guidewire in a first condition.
Figure 7:
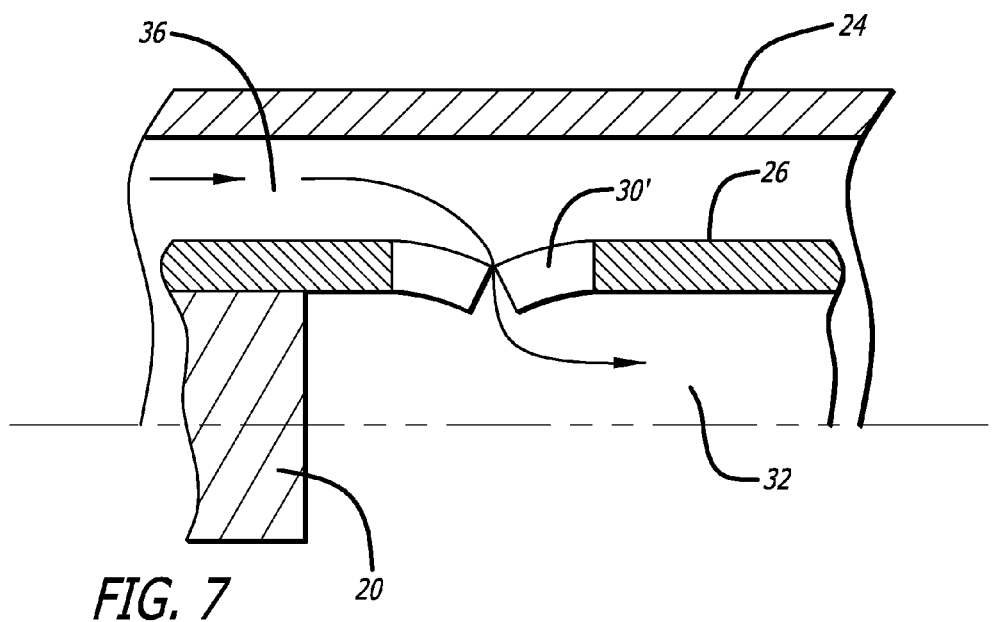
FIG. 7 is the detail view of FIG. 6 shown with a guidewire in a second condition.

Turning now to two optional embodiments of the slitted openings 30' as described above: As noted, the slitted openings may be configured to be either normally closed, or normally open.

Where the openings are configured to be normally closed, the fluid in the outer lumen 36 will tend to be blocked by the leaves 31' of the openings 30'. However, if the leaves tend to leak even in the closed condition under some pressure, the guidewire may be positioned distally in the first condition to assist in the blocking and prevention of any fluid flow through the openings 30'. When the guidewire is withdrawn proximally to the second condition, the fluid may be pressurized sufficiently to allow the fluid pressure to force the leaves inward to thus open the slitted openings 30', and the fluid may flow into the inner lumen 32 and thence out of the distal exit opening 34 as described above.

Where the openings 30' are configured to be normally open, (as may be envisaged with reference to FIG. 7 in which the leaves 31' reside normally in an inward position) and the guidewire is withdrawn proximally as in the second condition, the fluid in the outer lumen 36 is free to flow through the normally open slitted openings 30' into the inner lumen 32, and thence out of the distal exit 34. However should the treating physician wish to close off the openings and terminate the fluid flow, she may advance the guidewire distally to the first condition. The advancing guidewire forces the leaves 31' of the slitted openings 30' upwards to close the openings as may be envisaged with reference to FIG. 6.

Thus, the added feature of providing slitted openings (either normally open or normally closed) may assist in providing perforations that have added ability to be provide a better seal at desired stages of operation.

Thus, the configuration of the present invention allows the guidewire lumen 32 to have two functions, that can be altered by altering the condition, or position, of the guidewire 20.

Depending on the position of the guidewire 20: First, the guidewire lumen 32 may act to carry the guidewire 20 for placement of the catheter flexible portion 12. Second, the guidewire lumen 32 may act to allow contrast fluid to discharge from the very tip 29 of the catheter, at a location where the procedure is to be performed. This ability to switch uses of the guidewire lumen 32 by the simple means of adjusting the position of the guidewire has a considerable advantage over prior art devices in which perfusion openings have been provided along the external length of the distal end of a catheter, somewhat behind the tip of the catheter and not at the tip, thus giving rise to a cloud of contrast fluid at a location which is not at the very location of the procedure. The present invention overcomes this shortcoming by allowing the contrast fluid to discharge from the very tip of the catheter at the very location of the procedure.

In some embodiments, the catheter may include an outer cylinder 24 that defines a plurality of openings 33' that are configured to permit contrast fluid to flow from the second cylinder 24 to a space external to the second cylinder. Such an arrangement may be utilized where additional contrast fluid is required. In some embodiments, the openings may have a slitted form, and are configured to be normally closed. In other embodiments, the openings may be circular.

Thus, the catheter provides an advantageous structure for reducing the outside dimension of a catheter, by using lumens within the catheter for multiple functions. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

We claim:

1. A catheter comprising:
   a. a first lumen for receiving a guidewire and having an exit opening at a distal tip of the catheter;
   b. a second lumen, adjacent the first lumen and separated from the first lumen by a common wall, the second lumen configured for receiving contrast fluid, wherein perforations are formed in the common wall, the perforations each being defined by flexible leaves which are configured to flex between a first normally open position in which the leaves extend into the first lumen to open the perforations to fluid flow, and a second position in which the leaves close the perforations to fluid flow;
   c. a guidewire in the first lumen, the guidewire being configured to be capable of advancement distally to extend out of the exit opening, the guidewire having two conditions:
      i. a first condition in which the guidewire is advanced distally to force the flexible leaves from the first position into the second position so as to close the perforations to fluid flow;
      ii. a second condition in which the guidewire is withdrawn proximally to permit the flexible leaves to assume the first position so as to open the perforations and to provide a fluid flow path from the second lumen into the first lumen and thence out of the exit opening.

2. The catheter of claim 1, wherein the first lumen is defined by an inner cylinder, the inner cylinder being received within an outer cylinder, and the second lumen is a space between the inner cylinder and the outer cylinder.

3. The catheter of claim 2, wherein the outer cylinder defines a plurality of openings that are configured to permit contrast fluid to flow from the second cylinder to a space external to the second cylinder.

4. The catheter of claim 3, wherein the openings have a slitted form defined by flexible leaves that are configured to be normally closed.

5. The catheter of claim 2, wherein the perforations follow a single helical path along the axis of the inner cylinder, in which each subsequent perforation is offset by a radial angle in relation to a preceding perforation.

6. The catheter of claim 5, wherein the radial angle of offset is 90 degrees.

7. The catheter of claim 1, wherein a seal is provided in the first lumen to block fluid flowing proximally in the first lumen.

8. The catheter of claim 7, wherein the seal is an O-ring seal.

9. A method of discharging fluid from a distal end of a catheter, comprising:
   a. advancing a guidewire distally through a first lumen of the catheter;
   b. advancing fluid distally through a second lumen of the catheter;
   c. initially, blocking a flow of the fluid from the second lumen into the first lumen via perforations defined by leaves in a wall separating the first lumen from the second lumen, wherein blocking the flow comprises advancing the guidewire distally and applying a force with the guidewire against the leaves so as to move the leaves from a normally open position extending into the first lumen to a closed position;
   d. then, unblocking the flow of fluid from the second lumen into the first lumen by withdrawing the guidewire proximally thereby to allow the leaves to assume the normally open position;
   e. causing the fluid to flow from the second lumen to the first lumen, and thence out of the distal end of the catheter.

* * * * *